US006789021B2

(12) United States Patent
Rendahl et al.

(10) Patent No.: US 6,789,021 B2
(45) Date of Patent: Sep. 7, 2004

(54) METHOD AND SYSTEM FOR DETECTION OF HYDROCARBON SPECIES IN A GAS

(75) Inventors: Craig S. Rendahl, Tucson, AZ (US); Theresa A. Foley, Delavan, WI (US)

(73) Assignee: SPX Corporation, Charlotte, NC (US)

( * ) Notice: Subject to any disclaimer, the term of this patent is extended or adjusted under 35 U.S.C. 154(b) by 0 days.

(21) Appl. No.: 10/075,389

(22) Filed: Feb. 15, 2002

(65) Prior Publication Data

US 2003/0069703 A1 Apr. 10, 2003

Related U.S. Application Data

(60) Provisional application No. 60/312,895, filed on Aug. 16, 2001.

(51) Int. Cl.[7] .............................................. G01N 27/26
(52) U.S. Cl. ............................ 702/22; 702/23; 702/30; 702/35; 702/130; 702/184; 73/863.01
(58) Field of Search ............................. 702/23, 30, 35, 702/24; 73/863.01, 23.31, 23.32, 31.06; 60/272; 250/339.13

(56) References Cited

U.S. PATENT DOCUMENTS

| 3,950,101 | A | 4/1976 | Dewey, Jr. ..................... 356/51 |
| 4,507,558 | A | 3/1985 | Bonne ........................ 250/345 |
| 4,771,176 | A | 9/1988 | Schiefer et al. ............. 250/339 |
| 4,953,390 | A | 9/1990 | Krempl et al. ................ 73/116 |
| 5,319,199 | A | 6/1994 | Stedman et al. ......... 250/338.5 |
| 5,373,160 | A | 12/1994 | Taylor ..................... 250/338.5 |
| 5,807,750 | A | 9/1998 | Baum et al. ................. 436/164 |
| 5,832,411 | A | 11/1998 | Schatzmann et al. ......... 702/23 |
| 6,109,095 | A | * 8/2000 | Addiego .................... 73/31.06 |
| 6,307,201 | B1 | * 10/2001 | Didomenico et al. .. 250/339.13 |

FOREIGN PATENT DOCUMENTS

| DE | 4136413 | 11/1991 |
| DE | 19947669 | 10/1999 |
| GB | 2132758 | 7/1984 |
| GB | 2228568 | 8/1990 |

OTHER PUBLICATIONS

Bureau of Automotive Repair; "On Road Emissions Measurement System (OREMS) Specifications"; OREMS Specifications–Version O, Jan. 28, 2002; 2002 California DCA/BAR.

Jimenez–Palacios, José Luis; "Understanding and Quantifying Motor Vehicle Emissions with Vehicle Specific Power and TILDAS Remote Sensing"; Massachusetts Institute of Technology, Feb. 1999.

* cited by examiner

*Primary Examiner*—Kamini Shah
(74) *Attorney, Agent, or Firm*—Baker & Hostetler LLP

(57) ABSTRACT

A method and system for measuring hydrocarbon content in a gas sample measures individual hydrocarbon concentrations in the gas sample and determines a total concentration based on the individual concentrations. The total concentration is validated and/or scaled by determining whether water interference may be occurring and either adjusting the total concentration or flagging the total concentration as invalid. The total concentration may also be adjusted to account for ambient conditions, such as temperature, pressure or relative humidity, as well as for potential double-counting of individual hydrocarbon species.

22 Claims, 2 Drawing Sheets

METHOD AND SYSTEM FOR DETECTION OF HYDROCARBON SPECIES IN A GAS

PRIORITY

This application claims priority to, and incorporates by reference in its entirety, the U.S. Provisional Patent Application entitled Method and System for Detection of Hydrocarbon Species in a Gas, having a Ser. No. of 60/312,895, filed Aug. 16, 2001.

FIELD OF THE INVENTION

The present invention relates generally to gas sensing systems and vehicle emission detection systems. More particularly, the present invention relates to a method and system for detecting and measuring various species of hydrocarbons in a gas, such as a vehicle exhaust. The measurements detected by the present invention can be used in vehicle emission testing and other emission sensing systems and processes.

BACKGROUND OF THE INVENTION

Current methods of determining whether a vehicle is compliant with emission standards include open path and closed path emissions measurement systems. In a closed path system, an emission sensor is directly connected to the vehicle, such as by insertion into a tailpipe. An open path vehicular emissions measurement system collects data by means other than a direct connection to the tailpipe, such as a remote sensor that analyzes the individual emission components as the vehicle drives by the sensor. Open path vehicle emission systems are often preferable to closed path systems because they can be used in numerous locations and do not require the vehicle to stop for testing.

It is known that vehicle exhaust contains many types of hydrocarbon compounds. Alkane compounds have only single carbon-carbon bonds. Alkene compounds have a carbon-carbon double bond, and alkyne compounds have a carbon-carbon triple bond. Aromatic compounds contain a six carbon ring with three carbon-carbon double bonds. The double bonds tend to shift within the ring, making the aromatic carbon ring somewhat resistant to destruction.

It is known that some exhaust hydrocarbon compounds also contain oxygen. Carbonyl compounds, which contain a carbon-oxygen double bond, are combustion products not found in the original fuel. If the carbon-oxygen double bond is located on the end carbon of the hydrocarbon chain molecule, the compound is an aldehyde. If the carbon-oxygen double bond is located in the middle of the carbon chain, the compound is classified as a ketone. The spectral properties of aldehydes and ketones are very similar.

Compounds containing oxygen, such as ethers and alcohols, are added to fuel because the oxygen increases the combustion efficiency and thereby reduces emissions. Ether compounds contain an oxygen atom bound to two carbon atoms. Methyl tertiary butyl ether (MTBE) is the most common ether additive. Alcohol compounds contain a single carbon-oxygen bond, and the oxygen atom is also bound to a hydrogen atom. Ethanol is the most common alcohol additive. Methanol is also blended with gasoline and used as an alternative fuel.

Current open path analysis systems determine the total hydrocarbon concentration by measuring the infrared absorption in the single carbon-hydrogen bond-stretching region. Typically, propane gas is used for calibration. However, some important exhaust species such as benzene and acetylene do not have any single carbon-hydrogen bonds. These species do not absorb in the same infrared region and thus are not measured by the current art open path emissions sensors. In addition, other aromatic and alkene species have only a few alkane groups and absorb less infrared energy than the propane standard. Consequently the current remote sensing technology generally underestimates the total hydrocarbon concentration by about fifty percent. Another problem with the current technology is water vapor interference, which especially occurs at 30 to 50 degrees Fahrenheit. Still another issue with the current art is that there is no means for correcting a gas emissions measurement for changes in ambient temperature and pressure through the sample path. Accordingly, it is desirable to provide an improved hydrocarbon measurement system as herein disclosed.

SUMMARY OF THE INVENTION

In accordance with a preferred embodiment of the present invention, a method of measuring hydrocarbon content in a gas includes the steps of measuring one or more individual hydrocarbon concentrations in a gas sample, determining a total concentration based on the measured individual concentrations, identifying whether water interference is present in the gas sample, and determining whether water concentrations exceeds the interference level. Preferably, the first and second determining steps described above includes grouping the individual hydrocarbon concentrations into one or more classes, summing the individual hydrocarbon concentrations within each of the classes to yield one or more class concentrations; and adding the class concentrations to yield the total concentration.

If the third determining step determines that the amount of water in any state of matter exceeds the interference level, the method preferably includes the additional step of relating the total concentration to water contamination. Also, if the third determining step determines that the amount of water interference exceeds a certain level, the method may include the additional step of reporting a water interference condition.

Optionally and preferably, the measuring step includes the technique of using an open path emission sensor to detect the intensity of a plurality of infrared spectra in the gas sample. The measuring step also includes measurements by one or more of the following sampling methodologies: non-dispersive infrared detection; dispersive infrared detection; non-dispersive ultraviolet detection; dispersive ultraviolet detection, and others. These sampling methodologies can employ differential optical absorption spectroscopy, and/or gas filter correlation methods of detection to determine a concentration of a gas of interest.

As an option, the method may include additional steps of scaling the total concentration to account for multiple counting of individual hydrocarbon species, adjusting at least one of the individual hydrocarbon concentrations to account for one or more ambient conditions, and/or adjusting the total hydrocarbon concentration to account for one or more ambient conditions.

The method includes a system for measuring the hydrocarbon content in a gas using either an open path or closed path emissions sensor capable of detecting a plurality of individual hydrocarbons in a gas sample, a processor, and a computer-readable carrier such as a memory medium. The computer-readable carrier contains program instructions that instruct the processor to perform the steps of receiving data corresponding to a plurality of individual hydrocarbon concentrations in a sample, determining a total concentration based on the plurality of individual concentrations, measuring water interference levels in the gas sample, and determining whether the water concentrations correspond to an interference condition. Optionally, the system also includes a transmitter that is capable of transmitting data corresponding to the total concentration.

Optionally and preferably, the computer program instructs the processor to perform the first determining step to group the individual hydrocarbon concentrations into a plurality of classes, to sum the individual hydrocarbon concentrations within each of the plurality of classes to yield a plurality of class concentrations, and to add the class concentrations to yield the total concentration. The total concentration is applied to a combustion equation that corrects for any dilution of a sample due to being exhausted into open air. Also optionally, when concentrations of water correspond to an interference condition, the program further instructs the processor to relate the total concentration to water contamination.

As an additional option, the system may include a sensor that receives data of ambient conditions. In accordance with this embodiment, the program instructions optionally and preferably instruct the processor to adjust the total concentration in response to the data of ambient conditions. Further, the emissions sensor and the processor may be linked by a communications link that allows data corresponding to a plurality of individual hydrocarbon concentrations to be transmitted by the emissions sensor to the processor via the communications link.

DESCRIPTION OF PREFERRED EMBODIMENTS OF THE INVENTION

Figure 1:
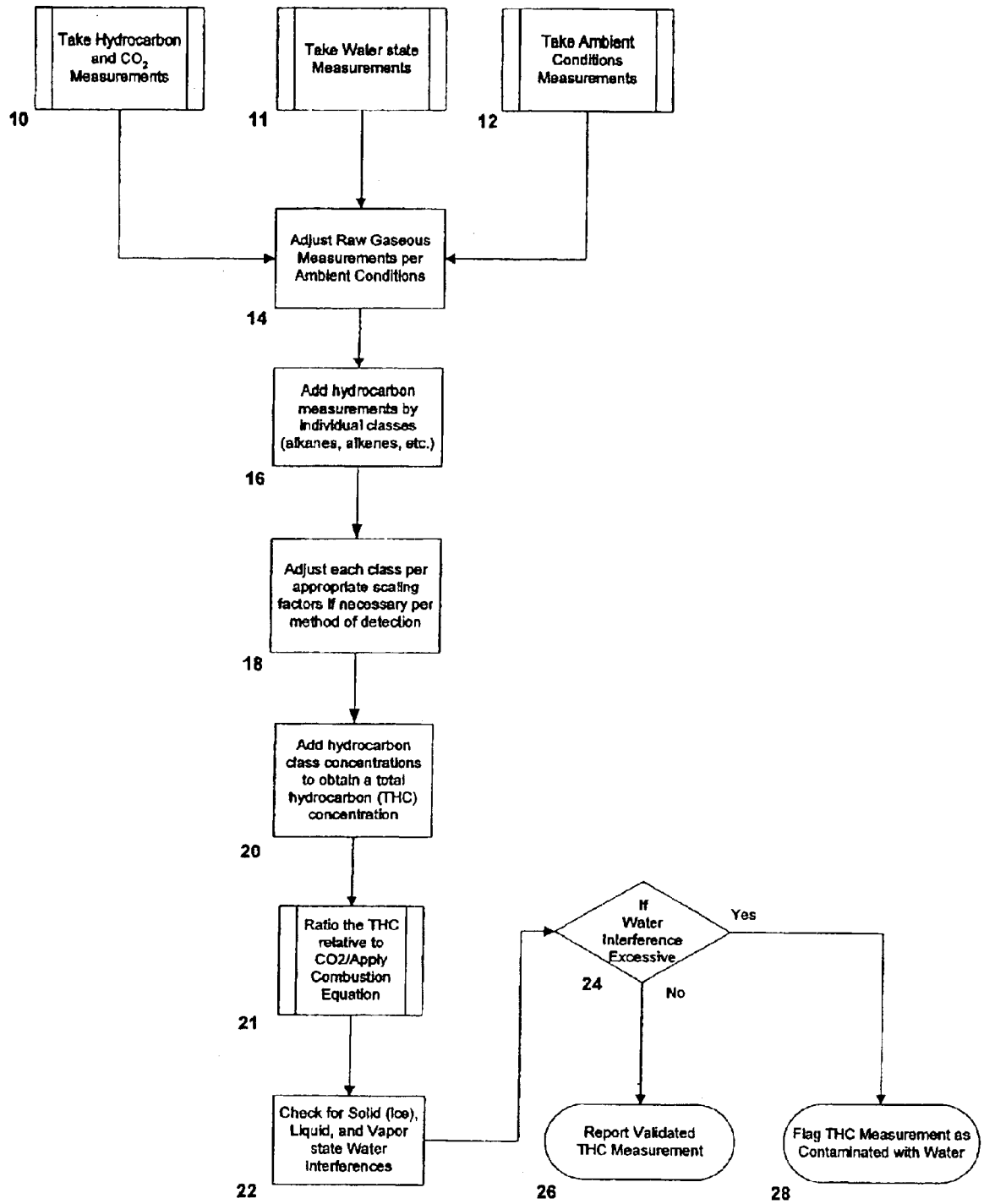
FIG. 1 is a block diagram illustrating exemplary steps of a preferred embodiment of the present inventive method.

A preferred embodiment of the present invention provides an improved hydrocarbon (HC) measurement system. FIG. 1 illustrates a preferred method embodiment of the present invention. The preferred embodiment as shown in FIG. 1 uses a method for measuring the total hydrocarbons of a gas, which may be referred to herein as summation by class, that includes the steps of taking HC specie concentration measurements and carbon dioxide ($CO_2$) measurements (step 10), preferably using an open path emission sensor utilizing technologies and methods of detection outlined below but optionally using a closed path emission sensor. Measurements of water (liquid and vapor states) (step 11), and optionally measurements of ice droplets in the HC sample are taken in the same time interval as HC specie and $CO_2$ concentration measurements (step 10) are made. Measurements of ambient conditions (step 12) including temperature, dew point or relative humidity, and barometric pressure are also taken in approximately the same time interval as that of the HC specie and $CO_2$ concentration measurements (step 10). Once all measurements are taken (steps 10, 11, 12), a correction for any non-linearity of measurements as applicable to the specific measuring device, correction for any variations in the output of the light source used to absorb and therefore detect HC species if this correction is not integral to the taking of HC specie and $CO_2$ measurements (step 10), and correction, perhaps to standard temperature and pressure, of HC specie and $CO_2$ measurements (step 10) per Ideal Gas Law as disclosed in prior art all define the correction actions taken in Step 14. Having corrected data from each HC sensor, add HC measurements by individual classes (e.g. alkanes+alkenes+alkynes+ benzene+carbonyl groups) (step 16); making adjustments to each class per appropriate scaling factors wavelength, as well as other factors as may be appropriate (step 18); and adding all of the adjusted HC class concentrations to get a total hydrocarbon (THC) measurement (step 20). In Step 21, the THC tailpipe measurement (steps 10, 11) is ratioed relative to $CO_2$ to correct for the dilution of tailpipe exhaust emitted into an open-path detection system, as disclosed in prior art. The undiluted concentrations of HC compounds are calculated using a combustion equation. It is this concentration that is reported from the embodiment, and can optimally be express in terms of a propane or hexane equivalent, whichever is desired.

Because water may interfere with individual HC measurements, especially alkene and alkyne group measurements, a check must be made to determine whether the THC measurement is indeed HC or if there is a significant water interference (step 22). This invention preferably determines the omni-state of water interference, which means that the interference for a given state of water is determined. For example, the invention in one embodiment measures and detects water (liquid and vapor states) (step 11), measures (step 11) or implies (step 22) detection of ice droplets in the HC sample, and flags and/or reports THC measurements that may be affected by liquid water contamination (step 28) and/or reports a validated THC measurement (step 26).

A list of wavelengths within the mid-infrared region used to measure water vapor are listed in Table 1. These wavelengths for the most part have interferences minimized, though $CO_2$ can interfere at the 2.75$\mu$ wavelength for open path systems in particular.

Typical vehicle exhaust will have approximately 20% water vapor content, and is a consequence of ideal combustion. What is important to this embodiment is what happens to the water vapor as it exits the exhaust system of a vehicle. Water vapor can condense into liquid water droplets and therefore interfere with HC species measurement. Alternatively, water vapor can sublimate into ice crystals also interfering with the detection of HC species.

TABLE 1

| Water Vapor Mid-Infrared Wavelengths |
| --- |
| Wavelength in microns ($\mu$) |
| 2.64 |
| 2.73 |
| 2.75 |
| 2.90 |
| 6.27 |

Omni-state water interference detection/interpretation will reduce the number of erroneously high hydrocarbon measurements that are caused by liquid water interference. Optionally and preferably, the liquid water interference is detected in part from ambient sensors, including a temperature sensor, pressure sensor, and/or relative humidity sensor (step 12), in combination with taking a water vapor measurement of the sample of HC gases (step 11). For example, liquid water interference is common if ambient temperatures are in the range of approximately 30 to 50 degrees Fahrenheit, or if ambient humidity is relatively high. Also, a vehicle that has not sufficiently warmed up can also emit excess water vapor, hence the desire for some means of measuring water vapor content (step 11) in the exhaust sample. The system may therefore optionally and preferably measure omni-state water interference (e.g. water in various states of matter) when such cool ambient conditions are present and measured in conjunction with water contamination emitted coincident with the HC species in tailpipe exhaust.

Very cold ambient temperatures can cause water vapor in tailpipe exhaust emissions to freeze into ice crystals almost immediately after exiting the tailpipe. The presence of ice crystals in an HC sample can cause erroneous HC measurements due to light scattering, in addition to interfering with the measurement of HC gases, by absorbing in similar wavelengths as the HC species of interest. Ice crystals can also cause interference with the measurement of particulate matter. Water in liquid (water droplets) and/or solid (ice) states of matter can be implied (step 22) with input from measured ambient conditions (step 12) through an algorithm that compares the amount of light attenuated at a reference wavelength where no HC species absorb light, against the amount of attenuation of light on each of the HC detection systems. A significant amount of attenuation on both the reference and HC detecting systems indicates a significant amount of water interference, particularly in certain ambient conditions, and can be noted in Step 22 of this preferred embodiment.

Measurement of, and correction for, ambient conditions is much less important for closed-path HC specie measurements embodiments than for open-path emissions measurements. This is especially true for embodiments that have a sample cell for the closed-path embodiment and the cell exists in a temperature and pressure controlled environment. However, open-path embodiments require ambient measurements (step 12) in order to make the desired corrections/adjustments to HC specie measurements (step 14).

In the present invention, a plurality of infrared measurements are needed. Preferably, at least four infrared measurements (one measurement for each class of hydrocarbons) are taken, at least one measurement of carbon dioxide ($CO_2$), and some method of taking a reference light measurement to determine the amount of light that is not absorbed in the gas sample. Some discrete ultraviolet measurements may also be made in order for scaling factor (step 18) and other corrections (step 14) and additions to the hydrocarbon group summations. The concentrations of the alkane, alkene, alkyne compounds as well as methane and HC measurements made in the infrared region of the spectrum are measured and summed to obtain a total hydrocarbon concentration (step 20). All of the oxygen containing compounds (carbonyls) are also alkane compounds and are included in the infrared alkane measurement (step 18). Aromatic compounds absorb in the same infrared region as alkene compounds along with methane and are included into these measurements (step 10). Therefore some scaling (step 18) is in order for these compounds depending upon the severity of the spectral overlap that is due to the method of detection employed to determine concentrations of HC species.

Table 2 is a sampling of various HC species found in vehicular tailpipe exhaust that may be measured and grouped into classes, along with the approximate wavelengths associated with measurement of each of the species. To even the casual observer, it is clear that several HC species of tailpipe emissions have absorption peaks that can appear in several places in the mid-infrared spectrum and that many HC specie absorb at the same wavelength. This is the fundamental reason behind specie overlap that occurs when commercially available broadband optical filters are used for sampling of HC species found in tailpipe emissions. This optical overlap is much less likely to occur for sampling methodologies that are not broadband, such as Dispersive InfraRed (DIR) measurements, Tunable Diode Lasers (TDL), and in some cases Gas Filter Correlation (GFC), which are all disclosed in other art. In each of these examples, the embodiments can look at more individual wavelengths of light and therefore not suffer the effects of interferences of one or more HC compound. Their disadvantage is that it is not practical to use these sampling methodologies when attempting to measure the 150 possible HC species that are emitted from gasoline-powered vehicles, because their narrow spectral range cannot capture all 150 possible HC species.

TABLE 2

Sample of HC Species, their Specie Groups, and Mid-Infrared Absorption Wavelengths

| COMPOUND | TYPE | WAVELENGTH ($\mu$) |
|---|---|---|
| Ethylene | Alkene | 3.22–3.35 |
| Propylene | Alkene | 3.24–3.34 |
| Acetylene | Alkyne | 3.04 |
| Methane | Alkane | 3.31 |
| Ethane | Alkane | 3.34–3.39 |
| Propane | Alkane | 3.36–3.51 |
| n-Butane | Alkane | 3.36–3.53 |
| n-Pentane | Alkane | 3.36–3.52 |
| n-Hexane | Alkane | 3.37–3.54 |
| Isobutane | Alkane | 3.38–3.53 |
| Isopentane | Alkane | 3.36–3.53 |
| 2,3-Dimethylbutane | Alkane | 3.36–3.45 |
| Benzene | Aromatic | 3.19–3.33 |
| Toluene | Aromatic | 3.14–3.68 |
| m-Xylene | Aromatic | 3.16–3.69 |
| p-Xylene | Aromatic | 3.15–3.73 |
| o-Xylene | Aromatic | 3.07–3.69 |
| 1,2,4-Trimethylbenzene | Aromatic | 3.13–3.75 |
| 1,3,5-Trimethylbenzene | Aromatic | 3.18–3.59 |
| Methanol | Alcohol | 3.36–3.54 |
| Ethanol | Alcohol | ~3.36–3.54 |
| MTBE | Ether | ~3.36–3.54 |
| Formaldehyde | Carbonyl | 5.73 (5.74) |
| Acetaldehyde | Carbonyl | 5.74 (5.75) |
| Propionaldehyde | Carbonyl | 5.75 |
| Butraldehyde | Carbonyl | 5.75 |
| Acrolein | Carbonyl | 5.83 |
| Methacrolein | Carbonyl | 5.84 |
| Crotonaldehyde | Carbonyl | 5.86 |
| Benzaldehyde | Carbonyl | 5.77 |
| Acetone | Carbonyl | 5.73 (5.80) |
| Butanone | Carbonyl | 5.72 |

The optical filter choices as listed in Table 3 can be used in order to economically sample for the various HC species of tailpipe exhaust, utilizing broadband optical filters to aggregate individual HC species into general chemical groups. Such broadband optical filters are best used for Non-Dispersive InfraRed (NDIR) sampling methodologies as disclosed in other art. A portion of the function of optical filter selection is determining what is commercially available. This can be limiting, as some commercial providers of filters may produce a filter with a bandpass broader or narrower than desired, creating more or less an opportunity for optical overlap.

A reference filter is also listed in Table 3, when an NDIR sampling methodology is used in combination with Differential Optical Absorption Spectroscopy (DOAS) method of detection, so that the preferred embodiment can sample for a period of time the amount of light from the embodiment that is not absorbed by any HC specie or interfering gas, then sample for roughly equal periods of time the amount of light absorbed by each of the specie groups. The DOAS method of detection has its roots in the Beer-Lambert Law, both of which are disclosed in other art.

TABLE 3

Preferred Mid-IR Optical Filter Choices for NDIR Methodology

| Specie Group | Channel | Principal Gas | Center of Bandpass | Bandpass Width |
|---|---|---|---|---|
| Alkane | $HC_1$ | Hexane ($C_6H_{14}$) | $3.46\mu$ | $0.200\mu$ |
| Alkene | $HC_2$ | Ethene ($C_2H_4$) | $3.23\mu$ | $0.090\mu$ |
| Alkyne | $HC_3$ | Acetylene ($C_2H_2$) | $3.04\mu$ | $0.070\mu$ |
| Methane | $HC_4$ | Methane ($CH_4$) | $3.31\mu$ | $0.060\mu$ |
| Reference | | No gas absorption | $3.90\mu$ | $0.110\mu$ |

The principal gas for each of these broadband filters of Table 3 is identified both for subsequent scaling factor activities disclosed below, and for identifying a suitable calibration gas for each of the broadband channels used in this embodiment. It is extremely important to have stable calibration gases that are commercially available in order to limit variability of the measurements and improve accuracy.

Carbonyl and aromatic compounds can be measured in the ultraviolet region. Table 4 lists HC species that may be measured and grouped into classes, along with the approximate ultraviolet wavelengths to measure each of the HC species. In some cases, the UV measured species are added to the Total HC measurement, and in other cases measurements are taken as part of scaling activities.

TABLE 4

HC Specie Absorption Identification in the UV Region

| COMPOUND | TYPE | WAVELENGTH (nanometers) |
|---|---|---|
| 1,3 Butadiene | Alkene | 209.5 |
| Benzene | Aromatic | 252.9 |
| Toluene | Aromatic | 266.6, 265 |
| m-Xylene | Aromatic | 270.6 |
| p-Xylene | Aromatic | 272.2 |
| o-Xylene | Aromatic | 269.0 |
| Ethylbenzene | Aromatic | 266.5 |
| Formaldehyde | Aldehyde | 325.0 |
| Acetaldehyde | Aldehyde | 285.0 |
| Acetone | Ketone | 278.0 |
| Propionaldehyde | Aldehyde | 293.0 |
| 2-Butanone | Aldehyde | 278.0 |
| Benzaldehyde | Aromatic Aldehyde | 284.1 |
| 2-Pentanenone | Carbonyl | 284.0 |
| o-Tolualdehyde | Aromatic Aldehyde | 292.2 |
| m-Tolueldehyde | Aromatic Aldehyde | 292.4 |
| p-Tolualdehyde | Aromatic Aldehyde | 285.5 |
| Phenol | Aromatic Alcohol | 275.1 |

Previous studies in chemical analysis have found that many HC compounds absorb in more than one infrared region. For example, propene contains both alkane and alkene functional groups and absorbs in both the alkane and alkene regions of the mid-infrared spectrum. This invention uses empirically determined scaling factors to eliminate multiple counting of species in the total hydrocarbon measurement (step 18).

Table 5 lists response factors of various classes of compounds that have absorption at the $3.45\mu$ wavelength, a wavelength where prior art has concentrated all NC measurements. This invention uses this wavelength for alkane group sampling. Except for methane and ethane, all of the alkane compounds listed in Table 5 have scaling factors close to one, which means that their NDIR response is very similar to their FID response. This invention measures methane at $3.31\mu$ and uses a scaling factor to subtract the absorption overlap of the methane and alkane optical filters. The same procedure could be used for ethane, although typical exhaust from gasoline-powered vehicles usually contains only a small percentage of ethane. The alkene and aromatic compounds also have much lower response factors at $3.45\mu$. This invention measures the alkene and aromatic compounds at wavelengths where their response is higher and uses scaling factors to subtract the overlap between the alkene and alkane optical filters.

TABLE 5

Response Factors for Select HC Species as Compared to FID Analysis

| COMPOUND | Measured Response using $3.45\mu$ Filter |
|---|---|
| Methane | 0.30 |
| Ethane | 0.81 |
| Propane | 1.00 |
| n-Hexane | 1.11 |
| 2-Methylbutane | 0.99 |
| 2-Methylpentane | 0.99 |
| 2,5-Dimethylhexane | 0.99 |
| 2,2,4-Trimethylpentane | 0.90 |
| Cyclopentane | 1.06 |
| Cyclohexane | 1.15 |
| Methylcyclopentane | 1.02 |
| Methylcyclohexane | 1.13 |
| Ethylene | 0.04 |
| Propene | 0.30 |
| Isobutene | 0.48 |
| 1-Hexene | 0.70 |
| Toluene | 0.15 |
| p-Xylene | 0.27 |
| 1,2,4-Trimethylbenzene | 0.43 |
| MTBE | 0.72 |
| Acetylene | (Zero) |

Scaling factors are used to calculate the optical absorption overlap between the various HC detection systems so that the total HC concentration is comparable to the total HC concentration measured by FID. These factors are more important the broader the optical bandpass filter used to measure HC species. For instance, it is likely that an optical filter centered at $3.46\mu$ with a bandpass cross-section of 200 nanometers will have an optical overlap with a filter centered at $3.31\mu$ and a bandpass cross-section of 60 nanometers. Both filters have an overlap region from $3.26\mu$ to $3.37\mu$ in varying energy levels. Couple this with the fact that many HC species have multiple absorption bands throughout the infrared spectrum. Methane has absorption bands in both of the example bandpass regions mentioned here.

For this reason, a permutation of likely scenarios exists for when scaling factors need to be applied in Step 18 to calculate a more accurate Total Hydrocarbon (THC) measurement. This permutation is outlined in Table 6. Scaling factors are calculated according to general formula in Equation 1.

TABLE 6

Scaling Factor Application Scenarios for this Embodiment

| Scenario # | Overlap Scenario |
| --- | --- |
| 1 | $HC_1$ with $HC_4$ |
| 2 | $HC_1$ with $HC_2$ |
| 3 | $HC_3$ with $HC_2$ |
| 4 | $HC_4$ with $HC_2$ |

Equation 1: General Scaling Factor Formula $$SF_{HCSpecie} = RF_{HCSpecie} \times WF_{HCSpecie}$$

where:

$SF_{HC\ specie}$ is the Scaling Factor for the HC specie of interest;

$RF_{HC\ Specie}$ is the Response Factor of the HC specie of interest by the preferred embodiment for the HC specie of interest;

$WF_{HC\ Specie}$ is the Weight Fraction of the given specie and expressed in a molar equivalent concentration or parts-per-million (ppm).

The total HC concentration in ppm can be estimated by multiplying the concentration of the alkane channel by two, as determined in prior studies. The multiplier of two was derived experimentally by stimulating current art open-path vehicular emissions testing equipment with typical exhaust compounds being emitted from a standard formulation of gasoline, then comparing the current art system's response with that of a Flame Ionization Detector (FID) response. This multiplier can range about the value of two, depending upon the formulation of the gasoline burned in the engine that causes the exhaust. The sum of the FID responses of all the exhaust compounds is equal to twice the response of the alkane channel (i.e. measuring total hydrocarbons at 3.45μ utilizing NDIR with DOAS methodology underestimates the FID response by 50%). This is important to open-path emissions detection systems whose data is compared to the results of a FID-type system. FID systems are commonly found in centralized, closed-path emissions testing facilities where motorists periodically are required to submit their vehicles to emissions compliance testing.

FID systems typically have been referred to as "carbon counter" systems due to the electrostatic method of detection. For this reason, molecular weights expressed in the following equations are in a "per carbon" basis and not the actual molecular weights for the referenced compounds in order to provide an equivalence to FID measurements. A "per carbon" expression means the effective molar weight per carbon of a carbon-hydrogen compound. For example, ethylene has a chemical formula of $C_2H_4$. The total weight of a mole of ethylene is 28 grams [(C=12)*2+(H=1)*4]. The per carbon basis for ethylene is 28 grams divided by two carbons to yield 14 grams/mole.

Equation 2: Calculation of Weight Fraction $$WF_{HCSpecies} = \frac{Weight_{Species}}{Weight_{THC}} = \frac{HC_x \times MW_{HC_x}}{FID_{adj} \times HC_y \times MW_{Exhaust}}$$

where:

$HC_x$ is the concentration of the HC specie or specie group $MW_{HCX}$ is the molecular weight of the HC species or specie group $FID_{adj}$ is the adjustment factor for measurements from this embodiment to agree with a Flame Ionization Detector (FID), and is typically 2.0 for standard formulation gasoline $HC_y$ is the concentration of alkanes $MW_{Exhaust}$ is the molecular weight of the exhaust The scaling factor calculation for the Alkene group of HC species assumes that ethylene is the major constituent showing absorption, a reasonable assumption because other Alkene compounds are found in exhaust at much lower concentrations:

Equation 3: General Scaling Factor Application Applied to Overlap Scenario #2 of $$SF_{ethylene} = RF_x \times WF_{HCSpecies} = \frac{0.04 \times [HC_x \times 14.0]}{[2.0 \times HC_y \times 14.0]}$$

where:

$SF_{ethylene}$ is representative of the Alkene group scaling factor.

$RF_x$ is the Response Factor, in this scenario for ethylene.

$WF_{HCSpecies}$ is the bracketed specifics commuted from Equation 2.

The constant "0.04" interpreted from Table 5 above for ethylene response factor.

Numerator "14.0" constant is the molecular weight of ethylene expressed in a per carbon basis grams/mole.

The constant "2.0" is the approximation scalar ($FID_{adj}$ from Equation 2) for the underrepresentation of the gasoline-powered exhaust total HC Specie at 3.45μ as compared to an FID type sensor. A different value might be employed if reformulated gasoline (RFG) is the fuel used to generate the exhaust. A representative value for typical RFG is 1.95.

Bracketed HC groups are expressed in parts-per-million (ppm) concentrations. $HC_x$ is the alkene concentration as measured by the ethylene filter and $HC_y$ is the alkane concentration.

Denominator "14.0" constant is the molecular weight of gasoline exhaust expressed in a per carbon basis grams/mole.

Correction of the raw alkane measurement is done by subtracting the overlap in optical absorption caused by an alkene compound(s) as seen in Equation 4.

Equation 4: General HC Specie Group Correction Formula Applied to Scenario #2

$$Alkane_{corrected} = Alkane_{measured} - (Alkene_{measured} \times SF_{ethylene})$$

Equation 5 provides a sample application of Equation 3, calculating the scaling factor for 100 ppm of measured alkenes using ethene (ethylene) as the indicator HC specie for the Alkene group, and assuming 100 ppm of measured alkanes.

Equation 5: Sample Scaling Factor Application for Alkene Group $$SF_{ethylene} = \frac{0.04 \times 100 \text{ ppm} \times 14.0 \text{ g/M}}{2.0 \times 100 \text{ ppm} \times 14.0 \text{ g/M}} = 0.02(no \cdot \text{units})$$

The ethylene scaling factor calculated in Equation 5 is plugged into Equation 4 to produce Equation 6, which subtracts the overlap between the alkene and alkane optical filters. This adjustment may seem trivial for the effort, however utilization of this embodiment for on-road emissions testing in "clean screen" scenarios is important, as the reason for a clean screen program is to exempt vehicles from regularly scheduled periodic emissions testing. A vehicle with low emissions, such as those which are candidates for a clean screen exemption, require emissions measurement systems that can make accurate and precise measurements of these small concentrations of tailpipe gases. Additionally, the on-road test needs to have a correlation with the emissions testing equipment that can be found in the periodic emissions testing facilities, such as FID sampling methodology systems, or else the data collected from the on-road testing equipment utilized in clean screen scenarios will not be trusted to be indicative of real-world emissions from vehicles. This embodiment solves the problems of the current art not correlating well with periodic emissions test facility equipment because this embodiment captures most of the HC species found in tailpipe exhaust, and furthermore can scale out multiple measurement of the HC species that overlap into more than one broadband optical filter.

Equation 6: Sample Scaling Factor Adjustment to Alkane Group by Alkene Overlap $$Alkane_{corrected} = 100 \text{ ppm} - (100 \text{ ppm} \times 0.02) \times \frac{14.0 \text{ g/M}}{14.0 \text{ g/M}} = 98 \text{ ppm}$$

In another example, Equation 7 calculates the scaling factor scenario of Table 6. The scaling factor calculation for methane overlap in the Alkane group measurement assumes that methane is the major constituent showing absorption at this infrared wavelength. This assumption does not introduce much error because aromatic compounds that also absorb at this wavelength have similar response factors.

Equation 7: General Scaling Factor Application Applied to Overlap Scenario #1 of Table 6

$$SF_{methane} = RF_x \times WF_{HCSpecies} = \frac{0.30 \times [HC_x \times 16.0]}{[2.0 \times HC_y \times 14.0]}$$

where:

$SF_{methane}$ is representative of the Methane group scaling factor—has the added benefit to provide a non-methane total hydrocarbon measurement often sought by air pollution modelers.

The constant "0.30" interpreted from Table 5 above for methane response factor.

Numerator "16.0" constant is the molecular weight of methane expressed in a per carbon basis grams/mole.

The constant "2.0" is the approximation scalar as discussed in Equation 3 for the underrepresentation of Alkane group measurements as compared to an FID type sensor. A different value might be employed if reformulated gasoline (RFG) is the fuel used to generate the exhaust. A representative value for typical RFG is 1.95.

Bracketed HC groups are expressed in parts-per-million (ppm) concentrations. $HC_x$ is the methane concentration and $HC_y$ is the alkane concentration.

Denominator "14.0" constant is the molecular weight of gasoline exhaust expressed in a per carbon basis grams/mole.

Plugging in sample measurements for Methane and Alkane groups of 100 ppm each, we get a scaling factor for the Methane group of 0.15 as shown in Equation 8.

Equation 8: Sample Scaling Factor Application for Methane Group $$SF_{methane} = \frac{0.30 \times 100 \text{ ppm} \times 16.0 \text{ g/M}}{2.0 \times 100 \text{ ppm} \times 14.0 \text{ g/M}} = 0.17(no \cdot \text{units})$$

And similarly with the alkene correction to the alkane measurement, the scaling factor calculated for methane is used to correct the alkane value (Equations 9 and 10), albeit more significantly than in the alkene example of Equation 6. It should be noted that the uncorrected alkane measurement is always used in the scaling equations as demonstrated in these scenarios. However, the THC measurement is an accumulation of the corrections (Scenario #2 correction=2 ppm and Scenario #4 correction=17 ppm; total is 19 ppm for these examples).

Equation 9: General HC Specie Group Correction Formula Applied to Scenario #1

$$Alkane_{corrected} = Alkane_{measured} - (Methane_{measured} \times SF_{methane})$$

Equation 10: Sample Scaling Factor Adjustment to Alkane Group by Methane Overlap $$Alkane_{corrected} = 100 \text{ ppm} - (100 \text{ ppm} \times 0.17) = 83 \text{ ppm}$$

Figure 2:
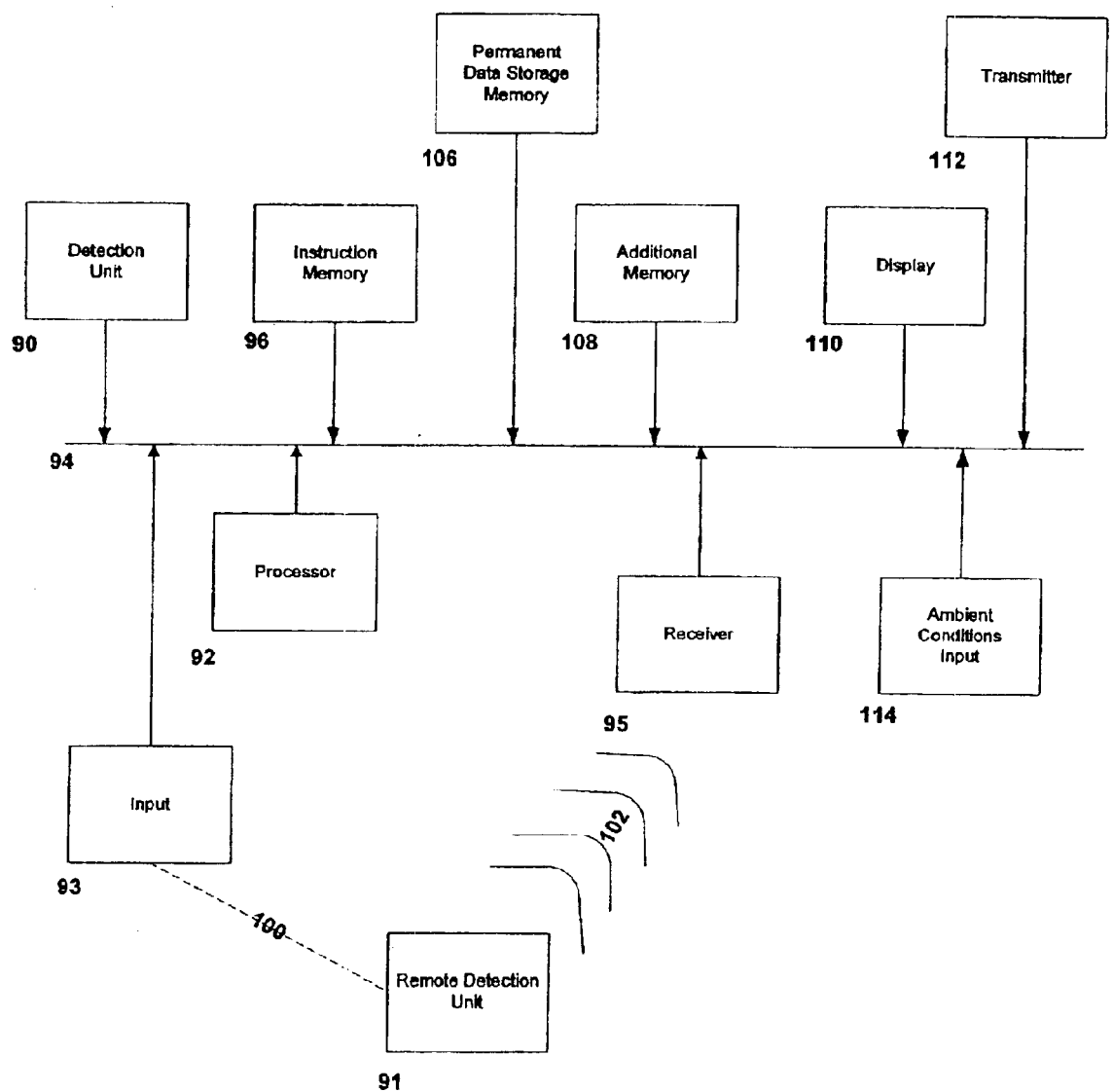
FIG. 2 illustrates several elements of a computer processing device and other components that may be used in a system embodiment of the present invention.

FIG. 2 illustrates several elements of a computer processing device that may be used to perform the steps described above. Referring to FIG. 2, a detection unit 90 delivers emissions-related data to a processor 92. The detection unit 90 may be any device that receives or contains information relating to HC emissions, such as an open path or closed path emissions sensor. Examples of detectors within a detection unit include discrete detectors with optical bandpass filters to measure a broad band of wavelengths of light specific to groups of HC species, broadband spectrometers to cover many absorption wavelengths, and tunable diode lasers designed to look at specific wavelengths and which can possibly jump-scan to several wavelengths in a short period of time ranging in milliseconds in length.

Any of these examples of detectors can employ various methods of sampling. These include but are not limited to Non-Dispersive InfraRed (NDIR), Dispersive InfraRed (DIR), Non-Dispersive UltraViolet (NDUV), Dispersive UltraViolet (DUV), Tunable Diode Laser (TDL), Non-Dispersive Visible (ND-VIS), Dispersive Visible (D-VIS), and potentially β-Scatter sampling techniques. Each of these sampling methods can be used in open-path emissions testing equipment that can comprise this embodiment. These sampling methods can utilize scaling factors as discussed above to a greater or lesser degree when comparing emissions measurements from these methods against measurements of the same gases utilizing Flame Ionization Detection (FID) or Gas Chromatography (GC) method. The actual scaling factors used for one methodology (NDIR, DIR, NDUV, DUV, TDL, ND-VIS, D-VIS, or β-scatter), compared to the other methodologies such as FID or GC that are used as standards for measurements, are determined empirically by comparing their response to an FID system response for the same gas of interest. Furthermore, these sampling methods have been disclosed in other art and utilized in other fields of invention.

Each sampling method offers strengths and weaknesses that are more or less subject to interferences and overlap of other HC species. For instance, a DIR system with sufficient resolution between wavelengths will be less subject to specie overlap and will not require as much adjustment to data by scaling factor as suggested above, as opposed to an NDIR method that utilizes mid-infrared bandpass filters. A bandpass filter allows a broad range of wavelengths to pass through the filter which is good for complete coverage of an HC group (alkanes, alkenes, etc.), but is also more reliant on scaling factors to correct out multiple counting of HC species among more than one HC discrete detector. A TDL system can be set to look at individual absorption lines of a specie, and therefore preferably does not require any scaling factor correction. However, coverage of an HC group is diminished as only one specie can be covered at a time, limiting the HC speciation system to only a few wavelengths of interest before cost of the system overwhelms the utility of such a method. This may not be practical for embodiments that need to measure vehicle tailpipe exhaust that can have as many as 150 different HC species.

Differential Optical Absorption System (DOAS), and Gas Filter Correlation (GFC) methods of detection are employed to interpret the measurements made through the sampling methodologies listed above, and have their roots in the Beer-Lambert Law for determining a concentration of a gas in a fluid. Referring to FIG. 2, the processor 92 runs computer code stored in memory 96 that contains code based upon the Beer-Lambert Law, such that the signals from the detection unit 90 can be converted into concentrations of gases of interest. The memory 96 also contains computer code that conducts the operations disclosed in FIG. 1 that the processor 92 completes for each measurement of a vehicle's emissions.

In the embodiment illustrated in FIG. 2, the detection unit 90 is part of the unit that contains the processor 92, and the delivery of signals from the detection unit 90 is performed by a direct link such as a serial bus, parallel bus, or internal computer bus 94. However, the processor 92 and detection unit 90 may be separate, such as with the optional remote detection unit 91. When a remote detection unit is used, the data may be delivered to the processor 92 by a hardwired communications link 100 that delivers the data to an input port 93 such as a communications port. An optional wireless communications link 102 and receiver for such a wireless communication 95 are also illustrated in FIG. 2. The communications link 102 may be a wireless communications link, a network within the global communications network such as an Intranet on the Internet, or any other communications medium.

The system illustrated in FIG. 2 also includes a computer-readable carrier 106 which may be a memory such as a hard drive, random access memory and/or read only memory. This memory 106 stores the emissions measurements made by this embodiment for later recall, and stores information useful during the collection of emissions, such as the FID adjustment factor for the fuel typically in use by the vehicles that are tested by this embodiment. The processor 92 will use this stored information for accurate scaling of the total HC measurement and other operations that require permanently stored setup parameters. Other memory devices 108 such as a CD-ROM, CD-RW, DVD, floppy drive, ZIP® drive, compact flash compatible memory devices, or other memory device to make the data portable may also be included. The system also optionally and preferably includes a display 110 and/or a transmitter 112 for providing output to a user or another device.

Optionally and preferably, the system illustrated in FIG. 2 also includes one or more input devices 114 that receive ambient data, such as temperature date, barometric pressure, and/or relative humidity data. Preferably, the ambient data is also delivered to the processor 92 and/or one of the memory devices via the bus 94. The ambient data is used for making corrections and adjustments to emissions measurements as described above.

The many features and advantages of the invention are apparent from the detailed specification, and thus, it is intended to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of measuring hydrocarbon content in a gas, comprising:

measuring a plurality of individual hydrocarbon concentrations in a gas sample;

determining a total concentration based on the plurality of individual concentrations;

identifying an occurrence of water interference in the gas sample; and determining whether the occurrence of water interference exceeds an interference level.

2. The method of claim 1 wherein the first determining step comprises:

grouping the individual hydrocarbon concentrations into a plurality of classes;

summing the individual hydrocarbon concentrations within each of the plurality of classes to yield a plurality of class concentrations; and adding the class concentrations to yield the total concentration.

3. The method of claim 1 wherein the second determining step determines that the amount of an occurrence of water interference exceeds an interference level, and comprising the additional step of relating the total concentration to water contamination.

4. The method of claim 1 wherein the second determining step determines whether an omni-state of water amount exceeds an interference level, and further comprising the step of reporting at least one state of matter of water interference condition.

5. The method of claim 1 wherein the measuring step comprises using an open path emission sensor to detect the intensity of a plurality of infrared spectra in the gas sample.

6. The method of claim 1 wherein the measuring step comprises measuring by at least one of non-dispersive infrared detection, dispersive infrared detection, non-dispersive ultraviolet detection, dispersive ultraviolet detection, tunable diode laser, non-dispersive visible detection and dispersive visible detection.

7. The method of claim 1 wherein the measuring step comprises measuring by at least one of differential optical absorption detection and gas filter correlation detection.

8. The method of claim 1 comprising the additional step of scaling the total concentration to account for optical overlap of individual hydrocarbon species.

9. The method of claim 1 comprising the additional step of adjusting at least one of the individual hydrocarbon and $CO_2$ concentrations to account for one or more ambient conditions.

10. The method of claim 1 comprising the additional step of adjusting the total hydrocarbon concentration to account for one or more ambient conditions.

11. A system for measuring hydrocarbon content in a gas, comprising:
    an emissions sensor capable of detecting a plurality of individual hydrocarbons in a gas sample;
    a processor in communication with said emissions sensor; and
    a computer-readable carrier in communication with said processor, said computer-readable carrier containing program instructions that instruct the processor to perform the steps of:
        receiving data corresponding to a plurality of individual hydrocarbon concentrations in a sample;
        determining a total concentration based on the plurality of individual concentrations;
        measuring an occurrence of water interference in the gas sample; and
        determining whether the occurrence of water interference corresponds to an interference condition.

12. The system of claim 11 wherein the emissions sensor comprises an open path emissions sensor or a closed path emissions sensor.

13. The system of claim 11 wherein the program instructions that instruct the processor to perform the first determining step comprise instructions to:
    group the individual hydrocarbon concentrations into a plurality of classes;
    sum the individual hydrocarbon concentrations within each of the plurality of classes to yield a plurality of class concentrations; and
    add the class concentrations to yield the total concentration.

14. The system of claim 11 further comprising an ambient condition sensor that receives ambient condition data.

15. The system of claim 14 wherein the program instructions further instruct the processor to adjust the total concentration in response to the ambient condition data.

16. The system of claim 11 further comprising a transmitter that is capable of transmitting data corresponding to the total concentration.

17. The system of claim 11 wherein the emissions sensor and the processor are linked by a communications link that allows data corresponding to a plurality of individual hydrocarbon concentrations to be transmitted by the emissions sensor to the processor via the communications link.

18. The system of claim 11 wherein the program instructions further instruct the processor to, when an omni-state of water occurrence corresponds to an interference condition, relate the total concentration to at least one state of matter of water interference contamination.

19. A system for measuring hydrocarbon content in a gas, comprising:
    a means for detecting a plurality of individual hydrocarbons in a gas sample;
    a means for determining a total concentration based on the plurality of individual concentrations;
    a means for identifying an occurrence of water interference in the gas sample; and
    a means for determining whether said occurrence of water interference correspond to an interference condition.

20. The system of claim 19 wherein the means for determining a total concentration comprises:
    a means for grouping the individual hydrocarbon concentrations into a plurality of classes;
    a means for summing the individual hydrocarbon concentrations within each of the plurality of classes to yield a plurality of class concentrations; and
    a means for adding the class concentrations to yield the total concentration.

21. The system of claim 19 further comprising:
    a means for detecting one or more ambient conditions; and
    a means for adjusting gas measurements to account for one or more ambient conditions.

22. The system of claim 19 further comprising:
    a means for scaling gas measurements to account for multiple counting of individual hydrocarbon species;
    a means for adjusting at least one of the individual hydrocarbon and $CO_2$ concentrations to account for one or more ambient conditions; and
    a means for adjusting the total hydrocarbon concentration to account for one or more ambient conditions.

* * * * *